(12) United States Patent
Nyemscek et al.

(10) Patent No.: US 11,235,086 B2
(45) Date of Patent: Feb. 1, 2022

(54) PROCESSES FOR COATING INORGANIC PARTICLES WITH A PEPTIDE OR PROTEIN USEFUL FOR IMPROVING CELLULAR ACTIVITY RELATED TO BONE GROWTH

(71) Applicant: Cerapedics, Inc., Westminster, CO (US)

(72) Inventors: Jevon Nyemscek, Exton, PA (US); Jessica Stufflet, Exton, PA (US); Nicolas Roscioli, Exton, PA (US); Doug Millard, Exton, PA (US); Katherine Suzanne Davis, Boulder, CO (US); Nolan Chase Hannigan, Lakewood, CO (US); Tristan Stuart Barnes, Louisville, CO (US); Jerome Connor, Doylestown, PA (US)

(73) Assignee: Cerapedics, Inc., Westminster, CO (US)

( * ) Notice: Subject to any disclaimer, the term of this patent is extended or adjusted under 35 U.S.C. 154(b) by 0 days.

(21) Appl. No.: 16/281,749

(22) Filed: Feb. 21, 2019

(65) Prior Publication Data

US 2020/0030488 A1   Jan. 30, 2020

Related U.S. Application Data

(60) Provisional application No. 62/660,465, filed on Apr. 20, 2018, provisional application No. 62/634,159, filed on Feb. 22, 2018.

(51) Int. Cl.
| | | |
|---|---|---|
| *A61L 27/12* | (2006.01) | |
| *A61K 38/39* | (2006.01) | |
| *A61L 27/54* | (2006.01) | |
| *A61K 9/14* | (2006.01) | |
| *A61K 47/69* | (2017.01) | |

(52) U.S. Cl.
CPC .............. *A61L 27/12* (2013.01); *A61K 9/143* (2013.01); *A61K 38/39* (2013.01); *A61K 47/6927* (2017.08); *A61L 27/54* (2013.01)

(58) Field of Classification Search
None
See application file for complete search history.

(56) References Cited

U.S. PATENT DOCUMENTS

| | | | |
|---|---|---|---|
| 3,728,446 A | 4/1973 | Roberts et al. | |
| 4,530,942 A | 7/1985 | Dhabhar et al. | |
| 5,207,983 A | 5/1993 | Liebert et al. | |
| 5,354,736 A | 10/1994 | Bhatnagar | |
| 5,487,777 A | 1/1996 | Lundan et al. | |
| 5,635,482 A | 6/1997 | Bhatnagar | |
| 5,674,848 A | 10/1997 | Bhatnagar | |
| 5,681,873 A | 10/1997 | Norton et al. | |
| 5,910,315 A | 6/1999 | Stevenson et al. | |
| 5,922,025 A | 7/1999 | Hubbard | |
| 5,958,428 A | 9/1999 | Bhatnagar | |
| 6,030,635 A | 2/2000 | Gertzman et al. | |
| 6,203,573 B1 | 3/2001 | Walter et al. | |
| 6,214,368 B1 | 4/2001 | Lee et al. | |
| 6,268,348 B1 | 7/2001 | Bhatnagar | |
| 6,287,341 B1 | 9/2001 | Lee et al. | |
| 6,326,018 B1 | 12/2001 | Gertzman et al. | |
| 6,340,477 B1 | 1/2002 | Anderson | |
| 6,432,437 B1 | 8/2002 | Hubbard | |
| 6,485,751 B1 | 11/2002 | Wang | |
| 6,537,574 B1 | 3/2003 | Hubbard | |
| 6,537,589 B1 | 3/2003 | Chae et al. | |
| 6,630,153 B2 | 10/2003 | Long et al. | |
| 6,692,760 B2 | 2/2004 | Miyamoto et al. | |
| RE38,522 E | 5/2004 | Gertzman et al. | |
| 6,818,620 B2 | 11/2004 | Bhatnagar | |
| 6,974,862 B2 | 12/2005 | Ringeisen et al. | |
| 7,060,287 B1 | 6/2006 | Hubbard et al. | |
| 7,628,851 B2 | 12/2009 | Armitage et al. | |
| 8,048,443 B2 | 11/2011 | Benedict et al. | |
| 9,101,694 B2 | 8/2015 | Benedict et al. | |
| 9,415,139 B2 | 8/2016 | Benedict et al. | |
| 2002/0018796 A1 | 2/2002 | Wironen | |
| 2002/0071827 A1 | 6/2002 | Petersen et al. | |

(Continued)

FOREIGN PATENT DOCUMENTS

| | | |
|---|---|---|
| WO | WO-86/01113 A1 | 2/1986 |
| WO | WO-03/063686 A2 | 8/2003 |

(Continued)

OTHER PUBLICATIONS

Extended European Search Report for European Application No. 17835086.4, dated May 15, 2020 (9 pages).
Atkinson et al., "Bioactive peptides may be covalently coupled to functionalised hydroxyapatite," eCM Meeting Abstracts 2016, Collection 1; Termis EU (p. P65).
Atkinson et al., "Evaluation of Hydrogel Carriers for Anorganic Bone Matrix/P-15," 82nd General Session & Exhibition of the IADR, March 10-13, Honolulu, Hawaii. (2004) (abstract of poster).
Bain, Jennifer Leigh, Dissertation: "Targeted Delivery of Osteoinductive Peptides to Bone Graft Utilizing a Calcium Binding Domain to Enhance the Regenerative Potential," Doctor of Philosophy, University of Alabama at Birmingham, 2014 (171 pages).

(Continued)

*Primary Examiner* — David J Blanchard
*Assistant Examiner* — Daniel F Coughlin
(74) *Attorney, Agent, or Firm* — Clark & Elbing LLP

(57) ABSTRACT

A method of coating a peptide or protein useful for improving the cellular activity related to bone growth on an inorganic particle comprises the steps of freezing the residual liquid present on uncoated and or coated inorganic particles, and drying the uncoated or coated inorganic particles after freezing the residual liquid, the drying comprising causing the frozen residual liquid to sublime under vacuum. Further disclosed embodiments of the invention include further processes for forming inorganic particles coated with a peptide or protein useful for improving cellular activity related to bone growth and medical devices comprising the coated particles.

12 Claims, No Drawings

Specification includes a Sequence Listing.

(56) References Cited

U.S. PATENT DOCUMENTS

| | | | |
|---|---|---|---|
| 2002/0192263 | A1 | 12/2002 | Merboth et al. |
| 2003/0009235 | A1 | 1/2003 | Manrique et al. |
| 2003/0077825 | A1 | 4/2003 | Bhatnagar et al. |
| 2003/0143283 | A1 | 7/2003 | Tofe |
| 2004/0062816 | A1 | 4/2004 | Atkinson et al. |
| 2004/0091462 | A1 | 5/2004 | Lin et al. |
| 2004/0185021 | A1 | 9/2004 | Hubbard |
| 2004/0197373 | A1 | 10/2004 | Gertzman et al. |
| 2004/0259972 | A1 | 12/2004 | Ringeisen et al. |
| 2005/0100533 | A1 | 5/2005 | Bhatnagar et al. |
| 2005/0118230 | A1 | 6/2005 | Hill et al. |
| 2005/0164944 | A1 | 7/2005 | Bhatnagar |
| 2005/0177238 | A1 | 8/2005 | Khandkar et al. |
| 2006/0173551 | A1 | 8/2006 | Hubbard et al. |
| 2006/0246397 | A1 | 11/2006 | Wolf |
| 2007/0041906 | A1 | 2/2007 | Lidgren et al. |
| 2007/0098799 | A1 | 5/2007 | Zhang et al. |
| 2007/0141103 | A1 | 6/2007 | Benedict et al. |
| 2009/0175944 | A1 | 7/2009 | Ringeisen et al. |
| 2011/0027332 | A1 | 2/2011 | Benedict et al. |
| 2011/0046686 | A1 | 2/2011 | Kaplan et al. |
| 2016/0095955 | A1 | 4/2016 | Benedict et al. |

FOREIGN PATENT DOCUMENTS

| | | | |
|---|---|---|---|
| WO | WO-2006/004778 | A2 | 1/2006 |
| WO | WO-2007/070681 | A2 | 6/2007 |
| WO | WO-2009/100280 | A2 | 8/2009 |
| WO | WO-2011/005510 | A2 | 1/2011 |
| WO | WO-2013/096797 | A2 | 6/2013 |
| WO | WO-2018/022553 | A1 | 2/2018 |

OTHER PUBLICATIONS

Communication for European Patent Application No. 06848598.6, dated Nov. 2, 2012 (7 pages).
Davies et al., "Optimization and Comparison of Three Vacuum Mixing Systems for Porosity Reduction of Simplex P Cement," Clin Orthop Relat Res. 1:261-269 (1990).
Delloye et al., "Bone substitutes in 2003: an overview," Acta Orthop Belg. 69(1):1-8 (2003).
Examination Report for Australian Application No. 2012358294, dated Dec. 11, 2015 (3 pages).
Examiner's Report for Australian Patent Application No. 2006326020, dated Jan. 5, 2012 (4 pages).
Extended European Search Report for European Application No. 06848598.6 dated Dec. 22, 2011 (6 pages).
Extended European Search Report for European Patent Application No. 12860704.1, dated Jan. 14, 2016 (8 pages).
Gelbart et al., "Maxillary Sinus Augmentation Using a Peptide-Modified Graft Material in Three Mixtures: A Prospective Human Case Series of Histologic and Histomorphometric Results," Implant Dent. 14:185-193 (2005).
Healos® Bone Graft Replacement, <http://www.medcompare.com/details/20376/Healos-Bone-Graft-Replacement.html>, retrieved on Jul. 13, 2012 (2 pages).
International Preliminary Report on Patentability for International Application No. PCT/US17/43614, dated Feb. 7, 2019 (9 pages).
International Preliminary Report on Patentability for International Patent Application No. PCT/US2012/071300, dated Dec. 2, 2014 (7 pages).
International Report on Patentability for PCT/US2006/047970, dated Nov. 27, 2008 (12 pages).
International Search Report and Written Opinion for International Application No. PCT/US17/43614, dated Dec. 22, 2017 (16 pages).
International Search Report and Written Opinion for International Application No. PCT/US2012/071300, dated Apr. 5, 2013 (16 pages).
International Search Report for International Application No. PCT/US2006/047970, dated Oct. 22, 2008 (1 page).
Manzano et al., "Comparison of the osteoblastic activity conferred on Si-doped hydroxyapatite scaffolds by different osteostatin coatings," Acta Biomater. 7(10):3555-62 (2011) (8 pages).
Nguyen et al., "Enhanced Cell Attachment and Osteoblastic Activity by P-15 Peptide-Coated Matrix in Hydrogels," Biochem Biophys Res Commun. 311(1):179-186 (2003).
Patel et al., "Autograft Versus P-15 in an Uninstrumented Sheep Lumbar Spine Fusion Model," The Spine Journal 7:8S (2007).
PTO-892 issued in U.S. Appl. No. 11/305,715 issued Aug. 22, 2011 (1 page).
Schrier et al., "Effect of a freeze-dried CMC/PLGA microsphere matrix of rhBMP-2 on bone healing," AAPS PharmSciTech. 2(3) 1-8 (2001).
Third Party Observation for International Patent Application No. PCT/US2017/043614, submitted Jul. 17, 2018 (2 pages).
Thorwarth et al., "Bioactivation of an Anorganic Bone Matrix by P-15 Peptide for the Promotion of Early Bone Formation," Biomaterials. 26(28):5648-5657 (2005).
U.S. Appl. No. 16/319,849, filed Jan. 23, 2019 (63 pages).
Vitoss Synthetic Cancellous Bone, http://www.orthovita.com/products/vitoss/index.html>, retrieved on Sep. 13, 2005 (4 pages).

PROCESSES FOR COATING INORGANIC PARTICLES WITH A PEPTIDE OR PROTEIN USEFUL FOR IMPROVING CELLULAR ACTIVITY RELATED TO BONE GROWTH

SEQUENCE LISTING

The instant application contains a Sequence Listing which has been submitted electronically in ASCII format and is hereby incorporated by reference in its entirety. Said ASCII copy, created on Oct. 8, 2019, is named 50517-030004 Sequence Listing 10.8.19 ST25 and is 4,565 bytes in size.

FIELD

The present inventions relate to processes for coating inorganic particles with a peptide or protein useful for improving the cellular activity related to bone growth, inorganic particles coated according to such processes, processes for preparing medical devices, and medical devices formed from such processes.

BACKGROUND

It is known to combine an inorganic material with a peptide or protein useful for improving cellular activity related to bone growth to enhance tissue healing, for instance in bone or tooth repair. The peptide may be structurally or biologically analogous to collagen and mimic the conformation recognized by collagen binding species, such as the P-15 region of collagen as disclosed in U.S. Pat. Nos. 5,635,482, 5,958,428, and 5,354,736. The P-15 region includes all or part of 15 amino acid residues, Gly-Thr-Pro-Gly-Pro-Gln-Gly-Ile-Ala-Gly-Gln-Arg-Gly-Val-Val (SEQ ID NO. 1), of the α1 (I) chain of collagen, and spans approximately residues 766-780 of this chain.

It is also known that acidic conditions promote solubility of certain endogenous bone morphogenic proteins (BMPs). See e.g. Zimmer COPIOS® Bone Void Filler product literature alleging "CopiOs Bone Void Filler provides a moderately acidic environment that promotes solubility of osteoinductive growth factors such as bone morphogenic proteins (BMPs)." See also Ugwu, Sidney et al., "The Effect of Buffers on Protein Conformational Stability," Pharmaceutical Tech., March 2004.

Further, Luca et al. concluded that "A trend towards higher mineralized bone formation (1.7-fold for CH, 1.4-fold for HY) was observed for rhBMP-2-loaded hydrogels at low pH (4.8±0.2) compared to high pH (6.2±0.2)." And that "This study also provided evidence that the formulation pH is a very important factor that may be critical to design efficient carriers for BMP-2." Luca Ludmila. et al. "The effects of carrier nature and pH on rhBMP-2-induced ectopic bone formation," Journal of Control Release, 1 Oct. 2010; 147(1): 38-44.

SUMMARY

Unfortunately, some of the more desirable inorganic particles for bone formation exhibit a high pH that makes them heretofore unusable in combination with a pH-sensitive peptides or proteins useful for improving cellular activity related to bone growth at industrial scale. It may be preferred that the inorganic particles are coated with the peptide or protein. It is not known how to efficiently and reliably coat inorganic particles with such peptides or proteins at an industrial scale such that the coated particles may be incorporated into a medical device with a high degree of quality, especially for certain high pH inorganic particles. Particles coated with the disclosed methods may exhibit a higher degree of peptide or protein adhesion and/or a higher degree of peptide or protein activity after the coating process than alternative methods. Additional improvements may relate to machinery reliability, uptime, and process speed.

Typically, an inorganic particle may be coated with a peptide or protein useful for improving cellular activity related to bone growth by first forming a solution comprising a coating buffer and the particles. Then, the peptide or protein useful for improving cellular activity related to bone growth is added, the mixture agitated, and the coating buffer drained. The coated particles may then be dried and packaged for use.

In accordance with the invention, a method of coating a peptide or protein useful for improving the cellular activity related to bone growth on an inorganic particle comprises the steps of freezing the residual liquid present on uncoated and or coated inorganic particles, and drying the uncoated or coated inorganic particles after freezing the residual liquid, the drying comprising causing the frozen residual liquid to sublime under vacuum. Further disclosed embodiments of the invention include further processes for forming inorganic particles coated with a peptide or protein useful for improving cellular activity related to bone growth and medical devices comprising the coated particles.

In an embodiment, the freezing is not primarily induced by evaporative cooling while cooling at a rate of at least −4° C./min. The prior art may utilize methods that substantially remove liquid from the inorganic particles in order to induce freezing through vacuum drying or other evaporative cooling means. This process will generally yield a slower process that may comprise additional process steps, may impact equipment reliability, and which may result in less peptide and/or protein bound to the surface of the inorganic particles.

DETAILED DESCRIPTION

Inorganic Particles

In an embodiment, the inorganic particles comprise ceramic particles. In an embodiment, the inorganic particles are of natural origin. In an embodiment, the inorganic particles are crystalline. In an embodiment, the inorganic particles are amorphous. In an embodiment, the inorganic particles comprise calcium phosphate particles or bioactive glass particles.

In an embodiment, the inorganic particles comprise calcium phosphate particles. Calcium phosphate particles are mineral particles comprising calcium and phosphate. In an embodiment, the calcium phosphate particles comprise particles of hydroxyapatite, tricalcium phosphate, tetracalcium phosphate, calcium pyrophosphate, calcium hydrogen phosphate, octacalcium phosphate, calcium fluorapatite, or a mixture thereof.

In an embodiment, the inorganic particles comprise a bioactive glass. Bioactive glasses are glass-ceramic particles. In an embodiment, the bioactive glass comprises $SiO_2$ and CaO. In an embodiment, the bioactive glass comprises at least 55 wt % $SiO_2$. In an embodiment, the bioactive glass comprises at least 28 wt % of CaO. In an embodiment, the bioactive glass further comprises $P_2O_5$. In an embodiment, the bioactive glass further comprises $Na_2O$. In an embodiment, the bioactive glass particles are sol-gel derived. In an embodiment, the bioactive glass particles are melt-derived.

In an embodiment, the inorganic particles comprise hydroxyapatite particles. In an embodiment, the hydroxyapatite particles comprise inorganic bone particles, in other words, bone particles with the organic material removed. The bone particles are typically derived from a human or animal source. Preferred animal sources are pigs and cows. For example, raw porcine or bovine bone particles may be subjected to chemical treatment and/or firing to remove organic matter, resulting in inorganic bone particles.

In an embodiment, the uncoated inorganic particles have a mean particle size of from 50 µm to 1000 µm. In an embodiment, the uncoated inorganic particles have a mean particle size of from 100 µm to 800 µm. In an embodiment, the uncoated inorganic particles have a mean particle size of from 300 µm to 700 µm. In an embodiment, 98% or greater of the uncoated inorganic particles have particles sizes of from 50 to 1000 µm. In an embodiment, 98% or greater of the uncoated inorganic particles have particles sizes of from 100 to 1000 µm. In an embodiment, 98% or greater of the uncoated inorganic particles have particles sizes of from 200 to 1000 µm.

Mean particle size and particle size distribution is measured by mechanical sieving with controlled sieves and a RO-TAP® sieve shaker which implements orbital motion with a downward tapping force.

In an embodiment, the inorganic particles have a porosity of at least 40%, at least 50%, or at least 60%. In an embodiment, the inorganic particles have a porosity of at most 80%, at most 75%, or at most 70%. Porosity is measured by MicoCT.

In an embodiment, the pH after 24 hours of a mixture of 10 mL phosphate buffered saline (PBS) having a pH of 7.43 and 0.5 g of the inorganic particles maintained at 20° C. is at least 8.0, at least 8.1, at least 8.2, at least 8.3, at least 8.4, at least 8.5, at least 8.6, at least 8.7, at least 8.8, at least 8.9, or at least 9.0. In an embodiment, the pH after 24 hours of a mixture of 10 mL phosphate buffered saline (PBS) having a pH of 7.43 and 0.5 g of the inorganic particles maintained at 20° C. is at most 11.0, at most 10.9, at most 10.8, at most 10.7, at most 10.6, at most 10.5, at most 10.4, at most 10.3, at most 10.2, at most 10.1, at most 10.0, at most 9.9, at most 9.8, at most 9.7, at most 9.6, at most 9.5, at most 9.4, at most 9.3, at most 9.2, at most 9.1, at most 9.0, at most 8.9, at most 8.8, or at most 8.7.

Peptide or Protein Useful for Improving Cellular Activity Related to Bone Growth In an embodiment, the peptide or protein useful for improving cellular activity related to bone growth comprises a peptide useful for improving cellular activity related to bone growth. In an embodiment, the peptide or protein useful for improving cellular activity related to bone growth consists of a peptide useful for improving cellular activity related to bone growth. The term peptide refers to a peptide of from 3 to 100 amino acid residues in length. In an embodiment, the peptide is at least 3, 4, 5, 6, 7, 8, 9, or 10 amino acid residues in length. In an embodiment, the peptide is at most 100, 95, 90, 85, 80, 75, 70, 65, 60, 55, 50, 45, or 40 amino acid residues in length.

In an embodiment, the peptide is a peptide that promotes the adhesion of cells, i.e. is a cell adhesion peptide. In an embodiment, the peptide promotes the adhesion of osteoblastic cells or precursors to osteoblastic cells, such mesenchymal stem cells. In an embodiment, the cell adhesion peptide is determined by screening peptide libraries for adhesion and selectivity to specific cell types or developed empirically via Phage display technologies.

In an embodiment, the cell adhesion peptide is a collagen mimetic peptide. The integrin α2β1 consists of two non-identical subunits, α2 and β1, members of the integrin family each with a single trans-membrane domain, and α2β1 is known to bind to collagen via a specialized region of the α2-subunit. There are several known α2βrecognition sites within collagens. This knowledge arises from the use of collagen fragments derived from purified α-chains cleaved into specific and reproducible peptides.

In an embodiment, the peptide is a collagen mimetic peptide that includes the peptide sequences of any of SEQ ID NOS. 1-21: Gly-Thr-Pro-Gly-Pro-Gln-Gly-Ile-Ala-Gly-Gln-Arg-Gly-Val-Val (SEQ ID NO. 1 "P-15"), Gly-Pro-Gln-Gly-Ile-Ala-Gly-Gln-Arg (SEQ ID NO: 2), Gln-Gly-He-Ala-Gly-Gln (SEQ ID NO: 3), Gln-Gly-Ile-Ala-Gly-Gln-Arg (SEQ ID NO: 4), Phe-Gly-Ile-Ala-Gly-Phe (SEQ ID NO: 5), Gly-He-Ala-Gly-Gln (SEQ ID NO: 6), Gln-Gly-Ala-Ile-Ala-Gln (SEQ ID NO: 7), Phe-Gly-He-Ala-Gly-Phe (SEQ ID NO: 8), Cys-Gly-He-Ala-Gly-Cys (SEQ ID NO: 9), Glu-Gly-Ile-Ala-Gly-Lys (SEQ ID NO: 10), N-Acetyl He-Ala-Ala (SEQ ID NO: 11), Ile-Ala-.beta.Ala (SEQ ID NO: 12), N-Acetyl He-Ala NMe (SEQ ID NO: 13), Asp-Gly-Glu-Ala (SEQ ID NO: 14), Asp-Gly-Glu-Ala-Gly-Cys (SEQ ID NO: 15), Gly-Phe-Pro'-Gly-Glu-Arg (SEQ ID NO: 16), Gly-Leu-Pro*-Gly-Glu-Arg (SEQ ID NO: 17), Gly-Met-Pro*-Gly-Glu-Arg (SEQ ID NO: 18), Gly-Ala-Ser-Gly-Glu-Arg (SEQ ID NO: 19), Gly-Leu-Ser-Gly-Glu-Arg (SEQ ID NO: 20), or Gly-Ala-Pro-Gly-Glu-Arg (SEQ ID NO: 21), wherein Pro* is hydroxyproline.

In an embodiment, the peptide or protein useful for improving cellular activity related to bone growth comprises a protein useful for improving cellular activity related to bone growth. In an embodiment, the peptide or protein useful for improving cellular activity related to bone growth consists of a protein useful for improving cellular activity related to bone growth. In an embodiment, the protein useful for improving cellular activity related to bone growth comprises a bone morphogenetic protein (BMP, such as BMP 1, BMP 3, BMP 4, and BMP 7), a transforming growth factor (e.g. a TGF-α or a TGF-β), a platelet-derived growth factor (PDGF), a platelet-derived angiogenesis factor (PDAF), a vascular endothelial growth factor (VEGF), a platelet-derived epidermal growth factor (PDEGF), a platelet factor 4 (PF-4), a fibroblast growth factor (FGF), an insulin-like growth factor (IGF, such as IGF-1 and IGF-2), β-thromboglobulin-related proteins (BTG), thrombospondins (TSP), or fibronectin, or a combination thereof.

In an embodiment, the protein comprises a FGF, TGF-β, IGF-2, PDGF, or BMP. In an embodiment, the protein comprises one or more selected from the group consisting of FGF, TGF-β, IGF-2, PDGF, BMP, and mixtures thereof.

In an embodiment, the peptide or protein useful for improving cellular activity related to bone growth is sensitive to a basic pH. In an embodiment, the peptide or protein useful for improving cellular activity related to bone growth is sensitive to a pH of 7 or more, 7.5 or more, 8 or more, 8.5 or more, 9 or more, or 9.5 or more, and less than a pH or 11 (e.g. a pH of from 7 to 11).

In an embodiment, the peptide or protein useful for improving cellular activity related to bone growth exhibits conformational instability at a basic pH. In an embodiment, the peptide or protein useful for improving cellular activity related to bone growth exhibits conformational instability at a pH of 7 or more, 7.5 or more, 8 or more, 8.5 or more, or 9 or more, and less than a pH of 11 (e.g. a pH of from 7 to 11). Conformational instability refers to unfolding, aggregation, denaturation, or inactivation of the peptide or protein. For example, a peptide or protein is conformationally instable at a pH that cause the peptide or protein to chelate on the surface of an inorganic particle in an inactive conformational form.

Process of Coating Inorganic Particles with Peptide or Protein

The disclosed processes for coating uncoated inorganic particles with a peptide or protein useful for improving cellular activity related to bone growth may comprise some combination of A. pre-treating uncoated inorganic particles, B. coating inorganic particles with a peptide or protein useful for improving cellular activity related to bone growth, and c. post-processing of the coated inorganic particles.

A. Pre-Treating Uncoated Inorganic Particles

In an embodiment, the inorganic particles are subjected to a pre-treatment prior to coating the inorganic particles with peptide or protein useful for improving cellular activity related to bone growth.

In an embodiment, the inorganic particles are first washed. In an embodiment, the inorganic particles are washed in a buffer solution. In an embodiment, the buffer solution is an aqueous buffer solution. In an embodiment, the buffer solution comprises PBS. In an embodiment, the buffer solution has a pH of from 7.0 to 10.0. In an embodiment, the buffer solution has a pH of from 7.0 to 8.0. The mixture of inorganic particles is agitated and the buffer solution drained. The process may be repeated multiple times, after which residual liquid is present in and/or on the uncoated inorganic particles.

In an embodiment, the residual liquid in and/or on the uncoated inorganic particles is frozen by putting the uncoated particles in a freezer. Typically, the uncoated inorganic particles are spread evenly onto a pan prior to freezing. In an embodiment, the mass of the uncoated inorganic particles frozen and dried in the process is at least 50 g, at least 100 g, at least 200 g, at least 500 g, at least 750 g, at least 1000 g, or at least 1200 g. In an embodiment, the mass of the uncoated inorganic particles frozen and dried in the process is at most 5000 g or at most 2000 g.

In an embodiment, the process comprises cooling the residual liquid present in and/or on the uncoated inorganic particles from ambient temperature to a temperature of 0° C. in less than 10 minutes, less than 9 minutes, less than 8 minutes, less than 7 minutes, less than 6 minutes, less than 5 minutes, less than 4.5 minutes, less than 4 minutes, less than 3.5 minutes, less than 3 minutes, less than 2.5 minutes, or less than 2 minutes. In an embodiment, this is accomplished by placing the uncoated particles in a blast freezer set at −30° C. or less, such as −40° C. In an embodiment, the residual liquid present in and/or on the uncoated inorganic particles is cooled from ambient temperature to a temperature of 0° C. or less in greater than 0.5 minutes, greater than 1 minute, or greater than 1.5 minutes. In an embodiment, the uncoated inorganic particles are cooled at a rate of at least −4° C./min, −5° C./min, −10° C./min, −15° C./min, or −20° C./min. In an embodiment, the uncoated inorganic particles are cooled at a rate of at most −50° C./min, −40° C./min, −35° C./min, −30° C./min, or −25° C./min.

In an embodiment, the freezing is performed at ambient pressure. In an embodiment, the freezing utilizes both conductive and convective heat transfer. In an embodiment, the uncoated inorganic particles are frozen under vacuum.

In an embodiment, the freezing is performed without substantial evaporation of the residual liquid during the freezing process. In an embodiment, the mass of the uncoated inorganic particles after freezing (but before the step of drying the inorganic particles) is at least 50%, 60%, 70%, 80%, 85%, 90%, 95%, 96%, 97%, 98%, 99%, 99.5%, 99.6%, 99.7%, 99.8%, or 99.9% of the mass of the uncoated inorganic particles just prior to freezing. The percentage change in mass of the uncoated inorganic particles may be determined by weighing a tray of the uncoated inorganic particles just prior to freezing and then weighing the tray of frozen uncoated inorganic particles after freezing. The mass of the empty tray is subtracted from each value and the percentage change in mass of the uncoated inorganic particles is determined.

In an embodiment, the mass of the uncoated inorganic particles

In an embodiment, the uncoated inorganic particles are dried of residual material (i.e. the now-frozen residual liquid) after freezing. In an embodiment, the drying comprises reducing the pressure below ambient pressure.

In an embodiment, the uncoated inorganic particles are freeze-dried. In an embodiment, the residual liquid is first frozen, a vacuum is applied, and the uncoated inorganic particles dried by causing the residual material to sublime under vacuum. Applying a vacuum is synonymous with "pulling a vacuum" or similar terms, and does not refer to a space devoid of matter. In an embodiment, the uncoated inorganic particles are slowly warmed while being dried. In an embodiment, the vacuum is applied in combination with a condenser having a temperature of less than the temperature of the uncoated inorganic particles. For example, the steps may comprise removing the uncoated inorganic particles from a blast freezer at −10° C., loading the uncoated inorganic particles into a freeze-drier set at a temperature of −22° C., and beginning the normal drying cycle used in the freeze-drier.

B. Coating Inorganic Particles with Peptide or Protein

In an embodiment, the inorganic particles have been pre-treated according to a process described above.

In an embodiment, the process comprises combining uncoated inorganic particles with a coating buffer, thereby forming a first coating mixture. In an embodiment, the first coating buffer is an aqueous coating buffer. In an embodiment, the aqueous coating buffer comprises a salt.

In an embodiment, the aqueous coating buffer comprises a 4-(2-hydroxyethyl)-1-piperazineethanesulfonic acid (HEPES) buffer, N-Tris(hydroxymethyl)methyl-3-aminopropanesulfonic acid (TAPS) buffer, Diethanol glycine, Dihydroxyethylglycine (BHG, or Bicine) buffer, Tris(hydroxymethyl)aminomethane (Tris) buffer, N-(Tri(hydroxymethyl)methyl)glycine (Tricine) 3-[N-Tris(hydroxymethyl)methylamino]-2-hydroxypropanesulfonic acid (TAPSO) buffer, 2-[[1,3-dihydroxy-2-(hydroxymethyl)propan-2-yl]amino]ethanesulfonic acid (TES) buffer; 3-(N-morpholino)propanesulfonic acid (MOPS) buffer, piperazine-N,N'-bis(2-ethanesulfonic acid) (PIPES) buffer, phosphate buffer, or a mixture thereof. In an embodiment, the aqueous coating buffer comprises from 300 to 600 mM NaCl (e.g., 350±50, 400±50, 450±50, 500±50, or 550±50 mM NaCl).

In an embodiment, the aqueous coating buffer has an osmolarity value of between 400 and 1,200 mOsm (e.g., 500±100, 700±200, 900±200, or 1,100±100 mOsm). In an embodiment, the aqueous coating buffer has a pH of from 6.5, 6.6, 6.7, 6.8, 6.9, 7.0, 7.1, 7.2, 7.3, 7.4, or 7.5 to 8.0, 7.9, 7.8, 7.7, 7.6, 7.5, 7.4, or 7.3. In an embodiment, the aqueous buffer has a pH of from 7.0 to 7.4.

After forming the first coating mixture, the peptide or protein is added, thereby forming a second coating mixture. In an embodiment, the peptide or protein may be added by first weighing the peptide or protein and then mixing it with a small amount of coating buffer, and then adding this to the first coating mixture. The second coating mixture is then agitated. In an embodiment, the second coating mixture is agitated for at least 10 minutes, at least 20 minutes, at least 30 minutes, at least 60 minutes, at least 90 minutes, or at least 120 minutes. Resulting are coated inorganic particles in liquid.

Following agitation, the liquid is drained, leaving behind coated inorganic particles. In an embodiment, coating buffer is added to the coated inorganic particles and drained. The mixture may be agitated prior to draining. The steps of adding coating buffer, agitating, and draining may be repeated a plurality of times, such as 2, 3, 4, 5, 6, or 7 times. The coating buffer may be the same or different than the coating buffer that formed the basis of the first coating mixture. After draining, there will be residual liquid present in and/or on the coated inorganic particles. Additional washing steps may also occur.

C. Post-Processing of Peptide-Coated Inorganic Particles

In an embodiment, the coated inorganic particles are frozen following the drain of the liquid. Typically, the coated inorganic particles are spread evenly onto a pan prior to freezing. In an embodiment, the mass of the coated inorganic particles frozen and dried in the process is at least 50 g, at least 100 g, at least 200 g, at least 500 g, at least 750 g, at least 1000 g, or at least 1200 g. In an embodiment, the mass of the coated inorganic particles frozen and dried in the process is at most 5000 g or at most 2000 g.

In an embodiment, the process comprises cooling the residual present in and/or on the coated inorganic particles from ambient temperature to a temperature of 0° C. in less than 10 minutes, less than 9 minutes, less than 8 minutes, less than 7 minutes, less than 6 minutes, less than 5 minutes, less than 4.5 minutes, less than 4 minutes, less than 3.5 minutes, less than 3 minutes, less than 2.5 minutes, or less than 2 minutes. In an embodiment, this is accomplished by placing the coated particles in a blast freezer set at −40° C. In an embodiment, the residual liquid present in and/or on the coated inorganic particles is cooled from ambient temperature to a temperature of 0° C. or less in greater than 0.5 minutes, greater than 1 minute, or greater than 1.5 minutes. In an embodiment, the coated inorganic particles are cooled at a rate of at least −4° C./min, −5° C./min, −10° C./min, −15° C./min, or −20° C./min. In an embodiment, the coated inorganic particles are cooled at a rate of at most −50° C./min, −40° C./min, −35° C./min, −30° C./min, or −25° C./min.

In an embodiment, the freezing is performed at ambient pressure. In an embodiment, the freezing utilizes both conductive and convective heat transfer. In an embodiment, the coated inorganic particles are frozen under vacuum.

In an embodiment, the freezing is not primarily induced by evaporative cooling. In an embodiment, the freezing is performed without substantial evaporation of the residual liquid during the freezing process. In an embodiment, the freezing does not comprise evaporative cooling.

In an embodiment, the mass of the coated inorganic particles after freezing (but before the step of drying the inorganic particles) is at least 50%, 60%, 70%, 80%, 85%, 90%, 95%, 96%, 97%, 98%, 99%, 99.5%, 99.6%, 99.7%, 99.8%, or 99.9% of the mass of the coated inorganic particles just prior to freezing. The percentage change in mass of the coated inorganic particles may be determined by weighing a tray of the coated inorganic particles just prior to freezing and then weighing the tray of frozen coated inorganic particles after freezing. The mass of the empty tray is subtracted from each value and the percentage change in mass of the coated inorganic particles is determined. In an embodiment, the freezing maintains or substantially maintains the concentration of residual liquid present in and/or on the inorganic particles.

In an embodiment, the freezing comprises cooling by forced convection. An example of an apparatus that cools by forced convection is a blast freezer. In a blast freezer, cold air is forced over the article being frozen. In an embodiment, freezing is performed without pulling a vacuum.

In an embodiment, the coated inorganic particles are dried of residual material (i.e. the now-frozen residual liquid) after freezing. In an embodiment, the drying comprises reducing the pressure below ambient pressure.

In an embodiment, the coated inorganic particles are freeze-dried. In an embodiment, the residual liquid is first frozen, a vacuum is applied, and the coated inorganic particles dried by causing the residual material to sublime under vacuum. In an embodiment, the coated inorganic particles are slowly warmed while being dried. In an embodiment, the vacuum is applied in combination with a condenser having a temperature of less than the temperature of the coated inorganic particles. For example, the steps may comprise removing the coated inorganic particles from a blast freezer at −10° C., loading the coated inorganic particles into a freeze-drier set at a temperature of −22° C., and beginning the normal drying cycle used in the freeze-drier.

After freeze-drying, the lyophilized coated inorganic particles may be sieved, e.g. with a sieve shaker, packaged, and stored.

Coated Inorganic Particles

In an embodiment, the amount of the peptide or protein bound to the surface of the inorganic particles is at least 100, at least 200, at least 300, at least 400, at least 500, at least 600, at least 700, at least 800, at least 900, at least 1000 ng, at least 1500 ng, at least 2000 ng, at least 2500 ng, at least 3000 ng, at least 3500 ng, or at least 4000 ng of peptide and/or protein per gram of inorganic particles. In an embodiment, the amount of the peptide or protein bound to the surface of the inorganic particles is at most 5000, at most 4500, at most 4400, at most 4300, or at most 4200 ng of peptide and/or protein per gram of inorganic particles. In an embodiment, the amount of the peptide or protein bound to the surface of the inorganic particles is from 100 to 1500 ng of peptide and/or protein per gram of inorganic particles. In an embodiment, the amount of the peptide or protein bound to the surface of the inorganic particles is from 100 to 1000 ng of peptide and/or protein per gram of inorganic particles. In an embodiment, the amount of the peptide or protein bound to the surface of the inorganic particles is from 100 to 600 ng of peptide and/or protein per gram of inorganic particles. The amount of the peptide or protein bound to the surface of the inorganic particles is measured by enzyme-linked immunosorbent assay (ELISA).

In an embodiment, the inorganic particles have a lower mean particle size after the coating process. This is theorized to be a result of breakup of the inorganic particles during the coating process. In an embodiment, the coated inorganic particles have a mean particle size of from 10 μm to 1000 μm. In an embodiment, the coated inorganic particles have a mean particle size of from 100 μm to 1000 μm. In an embodiment, the coated inorganic particles have a mean particle size of from 100 μm to 700 μm. In an embodiment, the coated inorganic particles have a mean particle size of from 300 μm to 600 μm. In an embodiment, 98% or greater of the coated inorganic particles have particles sizes of from 50 to 1000 μm. In an embodiment, 98% or greater of the coated inorganic particles have particles sizes of from 100 to 1000 μm. In an embodiment, 98% or greater of the coated inorganic particles have particles sizes of from 200 to 1000 μm.

Medical Devices Comprising the Coated Inorganic Particles

In an embodiment, a medical device comprises the coated inorganic particles. In an embodiment, a medical device comprises a syringe comprising a mixture comprising the coated inorganic particles. In an embodiment, the medical device is a bone void filler.

In an embodiment, a medical device comprising the coated inorganic particles further comprises collagen. In an embodiment, the collagen comprises native, fibrous collagen. In an embodiment, the collagen comprises native, soluble collagen. In an embodiment, the collagen comprises non-enzymatically processed, acid-soluble collagen.

Acid-soluble collagen is characterized by being insoluble at normal physiological pH, but becomes more soluble at a pH of 4 or lower. Acid-soluble collagen that has been processed non-enzymatically is distinguishable from the more commonly produced enzymatically-processed form of soluble collagen, in that non-enzymatically-processed, acid-soluble collagen will dissociate at a pH below 4, but not at physiological pH (i.e., pH 6-9), and when wetted at a physiological pH, the non-enzymatically processed, acid-soluble collagen will imbibe fluid and swell as a hydrogel. The enzymatically-processed, acid-soluble collagen would not be as effective at preventing phase separation or dewatering when compressed as would occur when, for example, manipulated by kneading, or passed through a narrow opening by injection. The lubricity provided by the inclusion of the non-enzymatically processed, acid-soluble collagen, along with its ability to retain fluid, allows the coated inorganic particles to more readily move relative to each other, and may prevent clogging at an orifice when the composition is to be injected.

In an embodiment, the process further comprises the steps of forming a slurry comprising collagen, the coated inorganic particles, and a liquid, and freeze-drying the slurry. In an embodiment, the process further comprises cross-linking the collagen. Collagen may be cross-linked via methods known in the art, such as by the addition of a cross-linking agent, e.g. glutaraldehyde, or dehydrothermal cross-linking.

In an embodiment, the medical device consists of coated inorganic particles and collagen. In an embodiment, the medical device consists of coated inorganic particles and collagen in a weight ratio of from 50:50 to 95:5 coated inorganic particles to collagen.

In an embodiment, the medical device further comprises one or more of dextrans, polyethylene, polymethylmethacrylate (PMMA), carbon fibers, polyvinyl alcohol (PVA), poly(ethylene terephthalate)polyamide, or a bioactive glass.

In an embodiment, the medical device further comprises polymer microspheres. In an embodiment, the polymer microspheres comprise poly(lactic acid) or poly(lactic-co-glycolic) acid.

In an embodiment, the coated particles are suspended in a hydrogel carrier. Polysaccharides that may be utilized as a carrier include, for example, any suitable polysaccharide within the following classes of polysaccharides: celluloses/starch, chitin and chitosan, hyaluronic acid, alginates, carrageenans, agar, and agarose. Certain specific polysaccharides that can be used include agar methylcellulose, hydroxypropyl methylcellulose, carboxymethylcellulose, ethylcellulose, microcrystalline cellulose, oxidized cellulose, chitin, chitosan, alginic acid, sodium alginate, and xanthan gum.

The hydrogels will typically include a solvent to control the viscosity of the material. The solvent may be an alcohol or alcohol ester, including for example, glycerol, triacetin, isopropyl alcohol, ethanol, and ethylene glycol, or mixtures of these. The paste or gel can include other components, such as surfactants, stabilizers, or pH buffers. For example, a suitable gel or paste can be prepared using water, glycerin and sodium carboxymethylcellulose.

In an embodiment, the medical device further comprises a biologically active agent. In an embodiment, the composition material further comprises an angiogenic agent, an anti-bacterial agent, an antibiotic, an anti-fungal, an anti-inflammatory agent, an antioxidant, blood, a blood fraction, bone marrow aspirate, bone marrow aspirate concentrate, cells, a cellular concentrate, a drug, glycosaminoglycans, glycoproteins, a growth factor, a hormone, lipids, morphogens, nucleotides, a painkiller, a free (i.e. not coated on the inorganic particles) peptide, a free protein, a radioactive material, a steroid, a surfactant, a vitamin, yeast, or a combination thereof.

In an embodiment, the medical device further comprises a vitamin or a metabolite of a vitamin. In an embodiment, the medical device further comprises vitamin D or a metabolite thereof, such as calcitriol. In an embodiment, the medical device further comprises Vitamin C, metabolites of Vitamin C, Vitamin D, metabolites of Vitamin D, Vitamin K, metabolites of Vitamin K, or combinations thereof. In an embodiment, the biologically active agent is present in an amount of from $10^{-11}$ to $10^{-2}$ mol/L, based on the total volume of the medical device.

EXAMPLES

Example 1. Blast-Freeze Followed by Freeze-Dryer Vs. Evaporative Freeze Followed by Freeze-Dryer ABM (anorganic bone matrix) particles are pretreated in a Hypertonic (~460 mM NaCl) HEPES buffer, pH 7.2, at a 10:1 ratio (ml solution to g ABM) for 24 hours. This solution is decanted off after 24 hours. This wash is repeated with fresh solution for 1 hour or until there is no pH change upon exposure to fresh solution. The final wash solution is decanted and the ABM dried. The pretreatment step is performed with agitation of some kind (roller, rotation, etc.). The uncoated particles are then freeze-dried by either 1) freezing by blast-freeze, placing the frozen material into a freeze-drier already set to a temperature below freezing, and drying the material using the drying cycle of the freeze-drier (blast-freeze/freeze-dry), or by rapidly freezing by evaporative cooling by pulling a strong vacuum in the freeze-drier and drying the material using the drying cycle of the freeze-drier (evaporative-freeze/freeze-dry). The blast freeze is significantly faster at freezing than the evaporative freeze.

A P-15 peptide coating buffer (concentration depends on final desired P-15 coated on ABM) is made using hypertonic HEPES, pH 7.2. The pretreated ABM is coated using a 2:1 ratio (mL solution to g ABM) for 24 hours. This step is performed statically, with no agitation. After the 24 hour coating step, the solution is removed. The coated ABM is washed 6-12 times in a 10:1 ratio of solution to ABM using hypertonic HEPES buffer, pH 7.2. After the final wash, the coated ABM particles are freeze-dried by either 1) freezing by blast-freeze, placing the frozen material into a freeze-drier already set to a temperature below freezing, and drying the material using the drying cycle of the freeze-drier (blast-freeze/freeze-dry), or by rapidly freezing by evaporative cooling by pulling a strong vacuum in the freeze-drier and drying the material using the drying cycle of the freeze-drier (evaporative-freeze/freeze-dry).

Table 1 below shows the amount of bound P-15 peptide on the ABM particles as measured by ELISA.

TABLE 1

Example 1 Results

| Pre-Treatment | Post-Treatment | P-15 ng/g ABM |
|---|---|---|
| blast-freeze/freeze-dry | blast-freeze/freeze-dry | 260 |
| evaporative-freeze/freeze-dry | evaporative-freeze/freeze-dry | 80 |

The rapid freezing provided by the blast freeze resulted in significantly more peptide bound to the surface of the ABM.

Supplemental Description of Certain Exemplary Embodiments

1. A method of coating a peptide or protein useful for improving the cellular activity related to bone growth on an inorganic particle comprising the steps of:
   a. washing uncoated inorganic particles,
   b. substantially separating any liquid and the uncoated inorganic particles, thereby obtaining uncoated inorganic particles with residual liquid present in and/or on the inorganic particles,
   c. freezing the residual liquid present in and/or on the uncoated inorganic particles, wherein the uncoated inorganic particles are cooled at a rate of at least $-4°$ C./min and wherein freezing is not primarily induced by evaporative cooling,
   d. drying the uncoated inorganic particles after freezing the residual liquid, the drying comprising causing the frozen residual liquid to sublime under vacuum, thereby forming pre-treated uncoated inorganic particles,
   e. forming a first coating mixture comprising the pre-treated uncoated inorganic particles and a coating buffer,
   f. adding a peptide or protein useful for improving cellular activity related to bone growth to the first coating mixture, thereby forming a second coating mixture,
   g. agitating the second coating mixture, thereby forming coated inorganic particles in the second coating mixture,
   h. substantially separating the coated inorganic particles and any liquid.

2. A method of coating a peptide on an inorganic particle comprising the steps of:
   a. forming a first coating mixture comprising uncoated inorganic particles and a coating buffer,
   b. adding a peptide or protein useful for improving cellular activity related to bone growth to the first coating mixture, thereby forming a second coating mixture,
   c. agitating the second coating mixture, thereby forming coated inorganic particles in the second coating mixture,
   d. substantially separating the coated inorganic particles and any liquid, thereby obtaining coated inorganic particles with residual liquid present in and/or on the coated inorganic particles,
   e. freezing the residual liquid present in and/or on the coated inorganic particles, wherein the coated inorganic particles are cooled at a rate of at least $-4°$ C./min and wherein freezing is not primarily induced by evaporative cooling,
   f. drying the coated inorganic particles after freezing the residual liquid, the drying comprising causing the frozen residual liquid to sublime under vacuum.

3. The method of any one of the preceding exemplary embodiments, further comprising the steps of:
   a. washing uncoated inorganic particles,
   b. substantially separating any liquid and the uncoated inorganic particles, thereby obtaining uncoated inorganic particles with residual liquid present in and/or on the uncoated inorganic particles,
   c. freezing the residual liquid present in and/or on the uncoated inorganic particles, wherein freezing is not primarily induced by evaporative cooling,
   d. drying the uncoated inorganic particles after freezing the residual liquid, the drying comprising causing the frozen residual liquid to sublime under vacuum, thereby forming pre-treated uncoated inorganic particles.

4. The method of any one of the preceding exemplary embodiments further comprising the steps of:
   i. freezing the residual liquid present in and/or on the coated inorganic particles, wherein freezing is not primarily induced by evaporative cooling,
   j. drying the coated inorganic particles after freezing the residual liquid, the drying comprising causing the frozen residual liquid to sublime under vacuum.

5. The method of any one of the preceding exemplary embodiments, wherein the total mass of the uncoated inorganic particles is at least 50 g, at least 100 g, at least 200 g, at least 500 g, at least 750 g, at least 1000 g, or at least 1200 g.

6. The method of any one of the preceding exemplary embodiments, wherein the total mass of the uncoated inorganic particles is at most 5000 g or at most 2000 g.

7. The method of any one of the preceding exemplary embodiments, wherein the total mass of the coated inorganic particles is at least 50 g, at least 100 g, at least 200 g, at least 500 g, at least 750 g, at least 1000 g, or at least 1200 g.

8. The method of any one of the preceding exemplary embodiments, wherein the total mass of the coated inorganic particles is at most 5000 g or at most 2000 g.

9. The method of any one of the preceding exemplary embodiments, wherein the step of washing uncoated inorganic particles comprises washing the uncoated inorganic particles in a buffer solution.

10. The method of any one of the preceding exemplary embodiments, wherein the buffer solution is an aqueous buffer solution.

11. The method of any one of the preceding exemplary embodiments, wherein the buffer solution comprises PBS.

12. The method of any one of the preceding exemplary embodiments, wherein the buffer solution has a pH of from 7.0 to 10.0.

13. The method of any one of the preceding exemplary embodiments, wherein the buffer solution has a pH of from 7.0 to 8.0.

14. The method of any one of the preceding exemplary embodiments, wherein the step of washing uncoated inorganic particles comprises agitating the mixture of uncoated inorganic particles and buffer solution and draining the buffer solution.

15. The method of any one of the preceding exemplary embodiments, wherein freezing is performed at ambient pressure.

16. The method of any one of the preceding exemplary embodiments, wherein freezing utilizes both conductive and convective heat transfer.
17. The method of any one of the preceding exemplary embodiments, wherein the drying comprises reducing the pressure below ambient pressure.
18. The method of any one of the preceding exemplary embodiments, wherein the freezing is performed without substantial evaporation of the residual liquid during the freezing.
19. The method of any one of the preceding exemplary embodiments, wherein the freezing comprises cooling by forced convection.
20. The method of any one of the preceding exemplary embodiments, wherein the freezing is performed without pulling a vacuum.
21. The method of any one of the preceding exemplary embodiments, wherein the freezing does not comprise evaporative cooling.
22. The method of any one of the preceding exemplary embodiments, wherein the freezing maintains the concentration of residual liquid present in and/or on the inorganic particles.
23. The method of any one of the preceding exemplary embodiments, wherein the freezing substantially maintains the concentration of residual liquid present in and/or on the inorganic particles.
24. The method of any one of the preceding exemplary embodiments, wherein the mass of the uncoated inorganic particles after freezing is at least 50%, 60%, 70%, 80%, 85%, 90%, 95%, 96%, 97%, 98%, 99%, 99.5%, 99.6%, 99.7%, 99.8%, or 99.9% of the mass of the uncoated inorganic particles just prior to freezing.
25. The method of the previous exemplary embodiment, wherein the percentage change in mass of the uncoated inorganic particles is determined by weighing a tray of the uncoated inorganic particles just prior to freezing, weighing the tray of frozen uncoated inorganic particles after freezing, subtracting from each the mass of the empty tray, and calculating the percentage change in mass.
26. The method of any one of the preceding exemplary embodiments, wherein the mass of the coated inorganic particles after freezing is at least 50%, 60%, 70%, 80%, 85%, 90%, 95%, 96%, 97%, 98%, 99%, 99.5%, 99.6%, 99.7%, 99.8%, or 99.9% of the mass of the coated inorganic particles just prior to freezing.
27. The method of the previous exemplary embodiment, wherein the percentage change in mass of the coated inorganic particles is determined by weighing a tray of the coated inorganic particles just prior to freezing, weighing the tray of frozen coated inorganic particles after freezing, subtracting from each the mass of the empty tray, and calculating the percentage change in mass.
28. The method of any one of the preceding exemplary embodiments, wherein the step of freezing the residual liquid comprises cooling the residual liquid present in and/or on the uncoated inorganic particles from ambient temperature to a temperature of 0° C. in less than 10 minutes, less than 9 minutes, less than 8 minutes, less than 7 minutes, less than 6 minutes, less than 5 minutes, less than 4.5 minutes, less than 4 minutes, less than 3.5 minutes, less than 3 minutes, less than 2.5 minutes, or less than 2 minutes.
29. The method of any one of the preceding exemplary embodiments, wherein the step of freezing the residual liquid is accomplished by placing the uncoated particles in a blast freezer.
30. The method of any one of the preceding exemplary embodiments, wherein the step of freezing the residual liquid is accomplished by placing the uncoated particles in a blast freezer set at −30° C. or less.
31. The method of any one of the preceding exemplary embodiments, wherein the residual liquid present in and/or on the uncoated inorganic particles is cooled from ambient temperature to a temperature of 0° C. or less in greater than 0.5 minutes, greater than 1 minute, or greater than 1.5 minutes.
32. The method of any one of the preceding exemplary embodiments, wherein the uncoated inorganic particles are cooled at a rate of at least −4° C./min, −5° C./min, −10° C./min, −15° C./min, or −20° C./min.
33. The method of any one of the preceding exemplary embodiments, wherein the uncoated inorganic particles are cooled at a rate of at most −50° C./min, −40° C./min, −35° C./min, −30° C./min, or −25° C./min.
34. The method of any one of the preceding exemplary embodiments, wherein the uncoated inorganic particles are frozen under vacuum.
35. The method of any one of the preceding exemplary embodiments, wherein the uncoated inorganic particles are freeze-dried.
36. The method of any one of the preceding exemplary embodiments, wherein the residual liquid is first frozen, a vacuum is applied, and the uncoated inorganic particles dried by causing the residual material to sublime under vacuum.
37. The method of any one of the preceding exemplary embodiments, wherein the uncoated inorganic particles are slowly warmed while being dried.
38. The method of any one of the preceding exemplary embodiments, wherein the vacuum is applied in combination with a condenser having a temperature of less than the temperature of the uncoated inorganic particles.
39. The method of any one of the preceding exemplary embodiments, wherein the steps of freezing and drying the uncoated inorganic particles comprises removing the uncoated inorganic particles from a blast freezer at −10° C. or less, loading the uncoated inorganic particles into a freeze-drier set at a temperature of −20° C. or less, and beginning the normal drying cycle used in the freeze-drier.
40. The method of any one of the preceding exemplary embodiments, wherein the step of forming a first coating mixture comprising uncoated inorganic particles and a coating buffer, comprises forming a first coating mixture comprising pre-treated uncoated inorganic particles.
41. The method of any one of the preceding exemplary embodiments, wherein the first coating buffer is an aqueous coating buffer.
42. The method of any one of the preceding exemplary embodiments, wherein the aqueous coating buffer comprises a salt.
43. The method of any one of the preceding exemplary embodiments, wherein the aqueous coating buffer comprises a 4-(2-hydroxyethyl)-1-piperazineethanesulfonic acid (HEPES) buffer, N-Tris(hydroxymethyl)methyl-3-aminopropanesulfonic acid (TAPS) buffer, Diethanol glycine, Dihydroxyethylglycine (BHG, or Bicine) buffer, Tris(hydroxymethyl)aminomethane (Tris) buffer, N-(Tri(hydroxymethyl)methyl)glycine (Tricine) 3-[N-Tris(hydroxymethyl)methylamino]-2-hydroxypropanesulfonic acid (TAPSO) buffer, 2-[[1,3-dihydroxy-2-(hydroxymethyl)propan-2-yl]amino]ethanesulfonic acid (TES) buffer; 3-(N-morpholino)propanesulfonic acid (MOPS) buffer, piperazine-N,N'-bis(2-ethanesulfonic acid) (PIPES) buffer, phosphate buffer, or a mixture thereof.

44. The method of any one of the preceding exemplary embodiments, wherein the aqueous coating buffer comprises from 300 to 600 mM NaCl (e.g., 350±50, 400±50, 450±50, 500±50, or 550±50 mM NaCl).

45. The method of any one of the preceding exemplary embodiments, wherein the aqueous coating buffer has an osmolarity value of between 400 and 1,200 mOsm (e.g., 500±100, 700±200, 900±200, or 1,100±100 mOsm).

46. The method of any one of the preceding exemplary embodiments, wherein the aqueous coating buffer has a pH of from 6.5, 6.6, 6.7, 6.8, 6.9, 7.0, 7.1, 7.2, 7.3, 7.4, or 7.5 to 8.0, 7.9, 7.8, 7.7, 7.6, 7.5, 7.4, or 7.3.

47. The method of any one of the preceding exemplary embodiments, wherein the aqueous buffer has a pH of from 7.0 to 7.4.

48. The method of any one of the preceding exemplary embodiments, wherein the second coating mixture is agitated for at least 10 minutes, at least 20 minutes, at least 30 minutes, at least 60 minutes, at least 90 minutes, or at least 120 minutes. Resulting are coated inorganic particles in liquid.

49. The method of any one of the preceding exemplary embodiments, further comprising adding coating buffer to the coated inorganic particles and drained after substantially separating the coated inorganic particles and the second coating mixture, optionally repeating these steps 2, 3, 4, 5, 6, or 7 times.

50. The method of any one of the preceding exemplary embodiments, wherein the step of freezing the residual liquid comprises cooling the residual liquid present in and/or on the coated inorganic particles from ambient temperature to a temperature of 0° C. in less than 10 minutes, less than 9 minutes, less than 8 minutes, less than 7 minutes, less than 6 minutes, less than 5 minutes, less than 4.5 minutes, less than 4 minutes, less than 3.5 minutes, less than 3 minutes, less than 2.5 minutes, or less than 2 minutes.

51. The method of any one of the preceding exemplary embodiments, wherein the step of freezing the residual liquid is accomplished by placing the coated particles in a blast freezer.

52. The method of any one of the preceding exemplary embodiments, wherein the step of freezing the residual liquid is accomplished by placing the coated particles in a blast freezer set at −30° C. or less.

53. The method of any one of the preceding exemplary embodiments, wherein the residual liquid present in and/or on the coated inorganic particles is cooled from ambient temperature to a temperature of 0° C. or less in greater than 0.5 minutes, greater than 1 minute, or greater than 1.5 minutes.

54. The method of any one of the preceding exemplary embodiments, wherein the coated inorganic particles are cooled at a rate of at least −4° C./min, −5° C./min, −10° C./min, −15° C./min, or −20° C./min.

55. The method of any one of the preceding exemplary embodiments, wherein the coated inorganic particles are cooled at a rate of at most −50° C./min, −40° C./min, −35° C./min, −30° C./min, or −25° C./min.

56. The method of any one of the preceding exemplary embodiments, wherein the coated inorganic particles are frozen under vacuum.

57. The method of any one of the preceding exemplary embodiments, wherein the coated inorganic particles are freeze-dried.

58. The method of any one of the preceding exemplary embodiments, wherein the residual liquid is first frozen, a vacuum is applied, and the coated inorganic particles dried by causing the residual material to sublime under vacuum.

59. The method of any one of the preceding exemplary embodiments, wherein the coated inorganic particles are slowly warmed while being dried.

60. The method of any one of the preceding exemplary embodiments, wherein the vacuum is applied in combination with a condenser having a temperature of less than the temperature of the coated inorganic particles.

61. The method of any one of the preceding exemplary embodiments, wherein the steps of freezing and drying the coated inorganic particles comprises removing the coated inorganic particles from a blast freezer at −10° C. or less, loading the coated inorganic particles into a freeze-drier set at a temperature of −20° C. or less, and beginning the normal drying cycle used in the freeze-drier.

62. The method of any one of the preceding exemplary embodiments, wherein the inorganic particles comprise calcium phosphate particles or bioactive glass particles.

63. The method of any one of the preceding exemplary embodiments, wherein the inorganic particles comprise calcium phosphate particles.

64. The method of any one of the preceding exemplary embodiments, wherein the inorganic particles comprise particles of hydroxyapatite, triinorganic, tetrainorganic, calcium pyrophosphate, calcium hydrogen phosphate, octainorganic, calcium fluorapatite, or a mixture thereof.

65. The method of any one of the preceding exemplary embodiments, wherein the inorganic particles comprise ceramic particles.

66. The method of any one of the preceding exemplary embodiments, wherein the inorganic particles are of natural origin.

67. The method of any one of the preceding exemplary embodiments, wherein the inorganic particles are crystalline.

68. The method of any one of the preceding exemplary embodiments, wherein the inorganic particles are amorphous.

69. The method of any one of the preceding exemplary embodiments, wherein the inorganic particles comprise hydroxyapatite particles.

70. The method of any one of the preceding exemplary embodiments, wherein the inorganic particles consist of hydroxyapatite particles.

71. The method of any one of the preceding exemplary embodiments, wherein the inorganic particles comprise bone particles.

72. The method of any one of the preceding exemplary embodiments, wherein the inorganic particles consist of bone particles.

73. The method of any one of the preceding exemplary embodiments, wherein the inorganic particles comprise inorganic bone particles.

74. The method of any one of the preceding exemplary embodiments, wherein the inorganic particles consist of inorganic bone particles.

75. The method of any one of the preceding exemplary embodiments, wherein the inorganic particles comprise bioactive glass particles.

76. The method of any one of the preceding exemplary embodiments, wherein the inorganic particles comprise the bioactive glass comprising $SiO_2$ and CaO.

77. The method of any one of the preceding exemplary embodiments, wherein the inorganic particles comprise bioactive glass comprising at least 55 wt % $SiO_2$.
78. The method of any one of the preceding exemplary embodiments, wherein the inorganic particles comprise bioactive glass comprising at least 28 wt % of CaO.
79. The method of any one of the preceding exemplary embodiments, wherein the inorganic particles comprise bioactive glass further comprising $P_2O_5$.
80. The method of any one of the preceding exemplary embodiments, wherein the inorganic particles comprise bioactive glass further comprising $Na_2O$.
81. The method of any one of the preceding exemplary embodiments, wherein the inorganic particles comprise bioactive glass particles that are sol-gel derived.
82. The method of any one of the preceding exemplary embodiments, wherein the inorganic particles comprise bioactive glass particles that are melt-derived.
83. The method of any one of the preceding exemplary embodiments, wherein the inorganic particles have a mean particle size of from 50 μm to 1000 μm.
84. The method of any one of the preceding exemplary embodiments, wherein the inorganic particles have a mean particle size of from 100 μm to 800 μm.
85. The method of any one of the preceding exemplary embodiments, wherein the uncoated inorganic particles have a mean particle size of from 300 μm to 700 μm.
86. The method of any one of the preceding exemplary embodiments, wherein 98% or greater of the uncoated inorganic particles have particles sizes of from 50 to 1000 μm.
87. The method of any one of the preceding exemplary embodiments, wherein 98% or greater of the uncoated inorganic particles have particles sizes of from 100 to 1000 μm.
88. The method of any one of the preceding exemplary embodiments, wherein 98% or greater of the uncoated inorganic particles have particles sizes of from 200 to 1000 μm.
89. The method of any one of the preceding exemplary embodiments, wherein the coated inorganic particles have a mean particle size of from 10 μm to 1000 μm.
90. The method of any one of the preceding exemplary embodiments, wherein the coated inorganic particles have a mean particle size of from 10 μm to 1000 μm.
91. The method of any one of the preceding exemplary embodiments, wherein the coated inorganic particles have a mean particle size of from 100 μm to 700 μm.
92. The method of any one of the preceding exemplary embodiments, wherein the coated inorganic particles have a mean particle size of from 300 μm to 600 μm.
93. The method of any one of the preceding exemplary embodiments, wherein 98% or greater of the coated inorganic particles have particles sizes of from 50 to 1000 μm.
94. The method of any one of the preceding exemplary embodiments, wherein 98% or greater of the coated inorganic particles have particles sizes of from 100 to 1000 μm.
95. The method of any one of the preceding exemplary embodiments, wherein 98% or greater of the coated inorganic particles have particles sizes of from 200 to 1000 μm.
96. The method of any one of the preceding exemplary embodiments, wherein the inorganic particles have a porosity of at least 40%, at least 50%, or at least 60%.
97. The method of any one of the preceding exemplary embodiments, wherein the inorganic particles have a porosity of at most 80%, at most 75%, or at most 70%.
98. The method of any one of the preceding exemplary embodiments, wherein the pH after 24 hours of a mixture of 10 mL phosphate buffered saline (PBS) having a pH of 7.43 and 0.5 g of the inorganic particles maintained at 20° C. is at least 8.0, at least 8.1, at least 8.2, at least 8.3, at least 8.4, at least 8.5, at least 8.6, at least 8.7, at least 8.8, at least 8.9, or at least 9.0.
99. The method of any one of the preceding exemplary embodiments, wherein the pH after 24 hours of a mixture of 10 mL phosphate buffered saline (PBS) having a pH of 7.43 and 0.5 g of the inorganic particles maintained at 20° C. is at most 11.0, at most 10.9, at most 10.8, at most 10.7, at most 10.6, at most 10.5, at most 10.4, at most 10.3, at most 10.2, at most 10.1, at most 10.0, at most 9.9, at most 9.8, at most 9.7, at most 9.6, at most 9.5, at most 9.4, at most 9.3, at most 9.2, at most 9.1, at most 9.0, at most 8.9, at most 8.8, or at most 8.7.
100. The method of any one of the preceding exemplary embodiments, wherein the peptide or protein useful for improving cellular activity related to bone growth comprises a peptide useful for improving cellular activity related to bone growth.
101. The method of any one of the preceding exemplary embodiments, wherein the peptide or protein useful for improving cellular activity related to bone growth consists of a peptide useful for improving cellular activity related to bone growth.
102. The method of any one of the preceding exemplary embodiments, wherein the peptide is from 3 to 100 amino acid residues in length.
103. The method of any one of the preceding exemplary embodiments, wherein the peptide is at least 3, 4, 5, 6, 7, 8, 9, or 10 amino acid residues in length.
104. The method of any one of the preceding exemplary embodiments, wherein the peptide is at most 100, 95, 90, 85, 80, 75, 70, 65, 60, 55, 50, 45, or 40 amino acid residues in length.
105. The method of any one of the preceding exemplary embodiments, wherein the peptide is a peptide is a cell adhesion peptide.
106. The method of any one of the preceding exemplary embodiments, wherein the peptide promotes the adhesion of osteoblastic cells or precursors to osteoblastic cells.
107. The method of any one of the preceding exemplary embodiments, wherein the cell adhesion peptide is determined by screening peptide libraries for adhesion and selectivity to specific cell types or developed empirically via Phage display technologies.
108. The method of any one of the preceding exemplary embodiments, wherein the cell adhesion peptide is a collagen mimetic peptide.
109. The method of any one of the preceding exemplary embodiments, wherein the peptide is a collagen mimetic peptide that includes the peptide sequences of any of SEQ ID NOS. 1-21: Gly-Thr-Pro-Gly-Pro-Gln-Gly-Ile-Ala-Gly-Gln-Arg-Gly-Val-Val (SEQ ID NO. 1 "P-15" 1, "P 15"), Gly-Pro-Gln-Gly-Ile-Ala-Gly-Gln-Arg (SEQ ID NO: 2), Gln-Gly-Ile-Ala-Gly-Gln (SEQ ID NO: 3), Gln-Gly-[pen Ile-Ala-Gly-Gln-Arg (SEQ ID NO: 4), Phe-Gly-He-Ala-Gly-Phe (SEQ ID NO: 5), Gly-Ile-Ala-Gly-Gln (SEQ II D NO: 6), Gln-Gly-Ala-Ile-Ala-Gln (SEQ ID NO: 7), Phe-Gly-He-Ala-Gly-Phe (SEQ ID NO: 8), Cys-Gly-He-Ala-Gly-Cys (SEQ ID NO: 9), Glu-Gly-Ile-Ala-Gly-Lys (SEQ ID NO: 10), N-Acetyl Ile-Ala-Ala (SEQ ID NO: 11), Ile-Ala-.beta.Ala (SEQ ID NO: 12), N-Acetyl Ile-Ala NMe (SEQ ID NO: 13), Asp-Gly-Glu-Ala (SEQ ID NO: 14), Asp-Gly-Glu-Ala-Gly-Cys (SEQ ID NO: 15), Gly-Phe-Pro'-Gly-Glu-Arg (SEQ ID NO: 16), Gly-Leu-Pro'-Gly-Glu-Arg (SEQ ID NO: 17), Gly-Met-Pro'-Gly-Glu-Arg (SEQ ID NO: 18), Gly-Ala-Ser-Gly-Glu-Arg (SEQ ID NO: 19), Gly-Leu-Ser-Gly-Glu-Arg (SEQ ID NO: 20), or Gly-Ala-Pro'-Gly-Glu-Arg (SEQ ID NO: 21), wherein Pro* is hydroxyproline.

110. The method of any one of the preceding exemplary embodiments, wherein the peptide or protein useful for improving cellular activity related to bone growth comprises a protein useful for improving cellular activity related to bone growth.

111. The method of any one of the preceding exemplary embodiments, wherein the peptide or protein useful for improving cellular activity related to bone growth consists of a protein useful for improving cellular activity related to bone growth.

112. The method of any one of the preceding exemplary embodiments, wherein the protein useful for improving cellular activity related to bone growth comprises a bone morphogenetic protein (BMP), a transforming growth factor (TGF), a platelet derived growth factor (PDGF), a platelet derived angiogenesis factor (PDAF), a vascular endothelial growth factor (VEGF), a platelet derived epidermal growth factor (PDEGF), a platelet factor 4 (PF 4), a fibroblast growth factor (FGF), an insulin like growth factor (IGF), β-thromboglobulin related proteins (BTG), thrombospondins (TSP), or fibronectin, or a combination thereof.

113. The method of any one of the preceding exemplary embodiments, wherein the protein comprises a FGF, TGF-β, IGF-2, PDGF, or BMP.

114. The method of any one of the preceding exemplary embodiments, wherein the protein comprises one or more selected from the group consisting of FGF, TGF-β, IGF-2, PDGF, or BMP, and mixtures thereof.

115. The method of any one of the preceding exemplary embodiments, wherein the peptide or protein useful for improving cellular activity related to bone growth is sensitive to a basic pH.

116. The method of any one of the preceding exemplary embodiments, wherein the peptide or protein useful for improving cellular activity related to bone growth is sensitive to a pH of 7 or more, 7.5 or more, 8 or more, 8.5 or more, 9 or more, or 9.5 or more, and less than a pH or 11.

117. The method of any one of the preceding exemplary embodiments, wherein the peptide or protein useful for improving cellular activity related to bone growth exhibits conformational instability at a basic pH.

118. The method of any one of the preceding exemplary embodiments, wherein the peptide or protein useful for improving cellular activity related to bone growth exhibits conformational instability at a pH of 7 or more, 7.5 or more, 8 or more, 8.5 or more, or 9 or more, and less than a pH of 11.

119. The method of any one of the preceding exemplary embodiments, wherein the amount of the peptide and/or protein bound to the surface of the inorganic particles is at least 100, at least 200, at least 300, at least 400, at least 500, at least 600, at least 700, at least 800, at least 900, at least 1000 ng, at least 1500 ng, at least 2000 ng, at least 2500 ng, at least 3000 ng, at least 3500 ng, or at least 4000 ng of peptide and/or protein per gram of inorganic particles.

120. The method of any one of the preceding exemplary embodiments, wherein the amount of the peptide and/or protein bound to the surface of the inorganic particles is at most 5000, at most 4500, at most 4400, at most 4300, or at most 4200 ng of peptide and/or protein per gram of inorganic particles.

121. The method of any one of the preceding exemplary embodiments, wherein the amount of the peptide and/or protein bound to the surface of the inorganic particles is from 100 to 1500 ng of peptide per gram of inorganic particles and/or protein.

122. The method of any one of the preceding exemplary embodiments, wherein the amount of the peptide and/or protein bound to the surface of the inorganic particles is from 100 to 1000 ng of peptide and/or protein per gram of inorganic particles.

123. The method of any one of the preceding exemplary embodiments, wherein the amount of the peptide and/or protein bound to the surface of the inorganic particles is from 100 to 600 ng of peptide and/or protein per gram of inorganic particles.

124. A process for forming a medical device comprising the steps of:
  a. obtaining coated inorganic particles by the method of any one of the previous exemplary embodiments,
  b. forming a slurry comprising collagen, a liquid, and the peptide-coating inorganic particles, and
  c. freeze-drying the slurry.

125. The process for forming a medical device according to the preceding exemplary embodiments, further comprising the step of cross-linking the collagen.

126. A composition comprising the peptide-coated ceramic particles produced by the method according to any one of the preceding exemplary embodiments.

127. A medical device comprising the composition according to the previous claim.

128. A medical device produced by the method of any one of the previous exemplary embodiments.

129. The medical device according to any one of preceding exemplary embodiments, wherein the medical device is a bone void filler.

130. The medical device according to any one of preceding exemplary embodiments, further comprising collagen.

131. The medical device according to any one of preceding exemplary embodiments, wherein the collagen comprises native, fibrous collagen.

132. The medical device according to any one of preceding exemplary embodiments, wherein the collagen comprises native, soluble collagen.

133. The medical device according to any one of preceding exemplary embodiments, wherein the collagen comprises non-enzymatically processed, acid-soluble collagen.

134. The medical device according to any one of preceding exemplary embodiments, further comprising one or more of dextrans, polyethylene, polymethylmethacrylate (PMMA), carbon fibers, polyvinyl alcohol (PVA), poly (ethylene terephthalate)polyamide, or a bioactive glass.

135. The medical device according to any one of preceding exemplary embodiments, further comprising polymer microspheres.

136. The medical device according to any one of preceding exemplary embodiments, further comprising polymer microspheres comprising poly(lactic acid) or poly(lactic-co-glycolic) acid.

137. The medical device according to any one of preceding exemplary embodiments, wherein the peptide-coated inorganic particles are suspended in a hydrogel carrier.

138. The medical device according to any one of preceding exemplary embodiments, further comprising a biologically active agent.
139. The medical device according to any one of preceding exemplary embodiments, further comprising a biologically active agent comprising an angiogenic agent, an anti-bacterial agent, an antibiotic, an anti-fungal, an anti-inflammatory agent, an antioxidant, blood, a blood fraction, bone marrow aspirate, bone marrow aspirate concentrate, cells, a cellular concentrate, a drug, glycosaminoglycans, glycoproteins, a growth factor, a hormone, lipids, morphogens, nucleotides, a painkiller, a free peptide, a free protein, a radioactive material, a steroid, a surfactant, a vitamin, yeast, or a combination thereof.
140. The medical device according to any one of preceding exemplary embodiments, further comprising a vitamin or a metabolite of a vitamin.
141. The medical device according to any one of preceding exemplary embodiments, further comprising vitamin D or a metabolite thereof.
142. The medical device according to any one of preceding exemplary embodiments, further comprising Vitamin C, metabolites of Vitamin C, Vitamin D, metabolites of Vitamin D, Vitamin K, metabolites of Vitamin K, or combinations thereof.
143. The medical device according to any one of preceding exemplary embodiments, further comprising a biologically active agent present in an amount of from $10^{-11}$ to $10^{-2}$ mol/L, based on the total volume of the medical device.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A method of coating an inorganic particle with a peptide or protein useful for improving cellular activity related to bone growth, the method comprising the steps of:
   a. washing uncoated inorganic particles,
   b. substantially separating any liquid and the uncoated inorganic particles, thereby obtaining uncoated inorganic particles with residual liquid present in and/or on the inorganic particles,
   c. freezing the residual liquid present in and/or on the uncoated inorganic particles, wherein the uncoated inorganic particles are cooled at a rate of at least −4° C./min and wherein freezing is not primarily induced by evaporative cooling,
   d. drying the uncoated inorganic particles after freezing the residual liquid, the drying comprising causing the frozen residual liquid to sublime under vacuum, thereby forming pre-treated uncoated inorganic particles,
   e. forming a first coating mixture comprising the pre-treated uncoated inorganic particles and a coating buffer,
   f. adding a peptide or protein useful for improving cellular activity related to bone growth to the first coating mixture, thereby forming a second coating mixture,
   g. agitating the second coating mixture, thereby forming coated inorganic particles in the second coating mixture,
   h. substantially separating the coated inorganic particles and any liquid.

2. A method of coating an inorganic particle with a peptide or protein comprising the steps of:
   a. forming a first coating mixture comprising uncoated inorganic particles and a coating buffer,
   b. adding a peptide or protein useful for improving cellular activity related to bone growth to the first coating mixture, thereby forming a second coating mixture,
   c. agitating the second coating mixture, thereby forming coated inorganic particles in the second coating mixture,
   d. substantially separating the coated inorganic particles and any liquid, thereby obtaining coated inorganic particles with residual liquid present in and/or on the coated inorganic particles,
   e. freezing the residual liquid present in and/or on the coated inorganic particles, wherein the coated inorganic particles are cooled at a rate of at least −4° C./min and wherein freezing is not primarily induced by evaporative cooling,
   f. drying the coated inorganic particles after freezing the residual liquid, the drying comprising causing the frozen residual liquid to sublime under vacuum.

3. The method of claim 1, wherein following step h. the method further comprises the steps of:
   i. freezing the residual liquid present in and/or on the coated inorganic particles, wherein freezing is not primarily induced by evaporative cooling,
   j. drying the coated inorganic particles after freezing the residual liquid, the drying comprising causing the frozen residual liquid to sublime under vacuum.

4. The method of claim 1, wherein the total mass of the uncoated inorganic particles is at least 50 g.

5. The method of claim 1, wherein the step of washing uncoated inorganic particles comprises washing the uncoated inorganic particles in an aqueous buffer solution.

6. The method of claim 5, wherein the buffer solution comprises PBS having a pH of from 7.0 to 10.0.

7. The method of claim 5, wherein the step of washing uncoated inorganic particles comprises agitating the mixture of uncoated inorganic particles and buffer solution and draining the buffer solution.

8. The method of claim 1, wherein the uncoated inorganic particles are cooled at a rate of at least −10° C./min.

9. The method of claim 1, wherein the inorganic particles comprise calcium phosphate particles.

10. The method of claim 1, wherein the inorganic particles comprise hydroxyapatite particles.

11. The method of claim 1, wherein the peptide or protein useful for improving cellular activity related to bone growth is a peptide.

12. The method of claim 1, wherein the peptide or protein useful for improving cellular activity related to bone growth is a cell adhesion peptide.

* * * * *

SEQUENCE LISTING

```
<160> NUMBER OF SEQ ID NOS: 21

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Gly Thr Pro Gly Pro Gln Gly Ile Ala Gly Gln Arg Gly Val Val
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Gly Pro Gln Gly Ile Ala Gly Gln Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 3

Gln Gly Ile Ala Gly Gln
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Gln Gly Ile Ala Gly Gln Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Phe Gly Ile Ala Gly Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Gly Ile Ala Gly Gln
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Gln Gly Ala Ile Ala Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Phe Gly Ile Ala Gly Phe
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9
```

```
Cys Gly Ile Ala Gly Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Glu Gly Ile Ala Gly Lys
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: ACETYLATION
<222> LOCATION: (1)..(1)
<223> OTHER INFORMATION: N-acetyl Isoleucine

<400> SEQUENCE: 11

Ile Ala Ala
1

<210> SEQ ID NO 12
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: beta.Ala

<400> SEQUENCE: 12

Ile Ala Ala
1

<210> SEQ ID NO 13
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: ACETYLATION
<222> LOCATION: (1)..(1)
<223> OTHER INFORMATION: N-acetyl Isoleucine
<220> FEATURE:
<221> NAME/KEY: METHYLATION
<222> LOCATION: (2)..(2)
<223> OTHER INFORMATION: alanyl-methylamide

<400> SEQUENCE: 13

Ile Ala
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct
```

```
<400> SEQUENCE: 14

Asp Gly Glu Ala
1

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Asp Gly Glu Ala Gly Cys
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is hydroxyproline

<400> SEQUENCE: 16

Gly Phe Xaa Gly Glu Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is hydroxyproline

<400> SEQUENCE: 17

Gly Leu Xaa Gly Glu Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is hydroxyproline

<400> SEQUENCE: 18

Gly Met Xaa Gly Glu Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19
```

```
Gly Ala Ser Gly Glu Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Gly Leu Ser Gly Glu Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is hydroxyproline

<400> SEQUENCE: 21

Gly Ala Xaa Gly Glu Arg
1               5
```